United States Patent
Lorch et al.

(10) Patent No.: US 10,213,336 B2
(45) Date of Patent: Feb. 26, 2019

(54) EYE DROP ASSIST APPARATUS

(71) Applicants: David Lorch, Ann Arbor, MI (US); Marius Tijunelis, Ann Arbor, MI (US)

(72) Inventors: David Lorch, Ann Arbor, MI (US); Marius Tijunelis, Ann Arbor, MI (US)

(73) Assignee: Ocunelis LLC, Ann Arbor, MI (US)

( * ) Notice: Subject to any disclaimer, the term of this patent is extended or adjusted under 35 U.S.C. 154(b) by 1200 days.

(21) Appl. No.: 14/485,959

(22) Filed: Sep. 15, 2014

(65) Prior Publication Data
US 2015/0088099 A1    Mar. 26, 2015

Related U.S. Application Data

(60) Provisional application No. 61/880,251, filed on Sep. 20, 2013.

(51) Int. Cl.
*A61H 33/04* (2006.01)
*A61F 9/00* (2006.01)
*A61M 35/00* (2006.01)
*B65D 37/00* (2006.01)
*B65D 47/18* (2006.01)

(52) U.S. Cl.
CPC .......... *A61F 9/0026* (2013.01); *A61F 9/0008* (2013.01); *B65D 47/18* (2013.01)

(58) Field of Classification Search
CPC ...... A61F 9/0026; A61F 9/0008; B65D 47/18
USPC ........ 604/302, 300, 289, 294, 295; 222/212, 222/420, 421
See application file for complete search history.

(56) References Cited

U.S. PATENT DOCUMENTS

| | | | |
|---|---|---|---|
| 2,676,592 A | | 4/1954 | Wood |
| 3,058,466 A | * | 10/1962 | Routsong .............. A61F 9/0026 604/302 |
| 3,521,636 A | | 7/1970 | Mahoney et al. |
| 3,934,590 A | | 1/1976 | Campagna et al. |
| 4,134,403 A | | 1/1979 | Johnsen et al. |
| 4,257,417 A | | 3/1981 | Gibilisco |
| 4,344,430 A | | 8/1982 | Astrove |
| 4,471,890 A | * | 9/1984 | Dougherty ............. B65D 47/18 222/190 |

(Continued)

FOREIGN PATENT DOCUMENTS

JP    2003235936 A    8/2003

*Primary Examiner* — Andrew J Mensh
(74) *Attorney, Agent, or Firm* — Endurance Law Group PLC (57) ABSTRACT

An eye drop assist apparatus and method for sequentially administering an ocular medication into a patient's eyes. A bottle or vial containing liquid eye drops is supported in a holder. First and second nasal locators extend in opposite directions from the holder. The nasal locators are separated by the pupillary distance (typically 60 mm), with the dispensing tip of the bottle located mid-way between. A person administering eye drops abuts the first nasal locator against the top of the patient's nasal bridge while aligning the tip of the bottle directly over a first eye before squeezing the bottle to forcibly expel one or more drops into the first eye. The person then linearly translates the bottle so that the second nasal locator abuts against the top of the patient's nasal bridge while aligning the tip of the bottle directly over a second eye. The bottle is then squeezed again to forcibly expel drops into the second eye.

18 Claims, 5 Drawing Sheets

(56) References Cited

U.S. PATENT DOCUMENTS

| | | | |
|---|---|---|---|
| 5,154,710 A | 10/1992 | Williams | |
| 5,387,202 A | 2/1995 | Baron | |
| 5,569,224 A | 10/1996 | Michalos | |
| 5,713,495 A * | 2/1998 | Menard | A61F 9/0026 222/212 |
| 6,371,945 B1 | 4/2002 | Sherman | |
| 6,530,908 B1 | 3/2003 | Sherman et al. | |
| 7,235,065 B1 * | 6/2007 | Sorensen | A61F 9/0008 604/294 |
| 8,348,912 B2 | 1/2013 | Rehkemper et al. | |
| 2009/0259204 A1 | 10/2009 | Galdeti et al. | |
| 2010/0286634 A1 * | 11/2010 | Marx | A61F 9/0026 604/302 |

* cited by examiner

EYE DROP ASSIST APPARATUS

CROSS REFERENCE TO RELATED APPLICATIONS

This application claims priority to Provisional Patent Application No. 61/880,251 filed Sep. 20, 2013, the entire disclosure of which is hereby incorporated by reference and relied upon.

BACKGROUND OF THE INVENTION

Field of the Invention

The invention relates generally to a device for administering liquid eye medication, and more particularly to an eye drop assist apparatus and method where a bottle containing liquid eye medication is supported for convenient one-handed operation.

Description of Related Art

Human eyes are susceptible to various forms of disease and distress which may, at times, require the administration of liquid medicines or other soothing agents. The placement of these liquid medications into the eye very often is accomplished by depositing one or more drops of medicated liquid from a small container or bottle directly onto the eye while the patient reclines their head. The prescribed eye drops are either self-administered by the patient or administered by a caregiver. Self-administered eye drops can sometimes prove a challenge for the patient and can result in wasted medication. Some patients have poor eyesight. The act of focusing on the dispensing tip of the bottle to ensure proper drop alignment can be difficult for such patients. Some patients have arthritis or other fine motor skill issues, such that it is difficult to hold and squeeze the bottle without assistance. Some patients have a natural fear associated with administering eye drops, in which case their body senses and muscles are in such an excited state of apprehension that placing eye drops may take several tries to receive the correct number of drops. These and other problems can be compounded when the patient is elderly, infirm or a juvenile.

In the conventional way to self-administer eye drops, the patient uses both hands—one to hold the bottle and the other free hand to pull down on the lower eyelid. The head is tilted back, and then the dispensing tip of the bottle is aligned over the eye so that a drop will fall directly onto the exposed eye, usually recommended into the conjunctival sac region. This process is often immediately repeated for the other (second) eye. An optimal distance between bottle tip and eye can be difficult for a patient to judge for themselves when self-administering eye drops. Too close, and the bottle tip may contact the exposed eye. Too far and the drop may not land in the intended place, possibly even missing the eye entirely. Thus, the conventional way to self-administer eye drops carries an elevated risk of wasting medication (by missed drops), of contaminating the eye and/or bottle tip (by inadvertent contact with the patient's eye), is cumbersome especially for self-administered applications, and may even be impractical for some patients.

The prior art has proposed various apparatus to aide in the administration of eye drops. Such apparatus are designed to support a typical eye drop bottle and provide alignment assistance to help make the process of self-administering eye drops more convenient. Examples of such prior art eye drop assist devices may be seen, for examples, in: U.S. Pat. No. 3,058,466 to Routsong issued Oct. 16, 1962; U.S. Pat. No. 5,154,710 to Williams issued Oct. 13, 1992; and US Patent Publication No. 2010/0286634 to Marx published Nov. 11, 2010. Generally stated, these apparatus include features designed to support the eye drop bottle in combination with a locator that establishes an offset distance from some reference point on the user (e.g., nose, forehead, cheek, or lower eyelid) so that the bottle tip positions itself directly over one eye. Specific examples of prior art apparatus that utilize the top (i.e., bridge) of a patient's nose may be seen in U.S. Pat. No. 3,934,590 to Campagna et al. issued Jan. 27, 1976; U.S. Pat. No. 4,134,403 to Johnsen et al. issued Jan. 16, 1979; U.S. Pat. No. 4,257,417 to Gibilisco issued Mar. 24, 1981; and U.S. Pat. No. 7,235,065 to Sorensen issued Jun. 26, 2007. In these examples, the locating feature takes the form of an inverted "V" designed to straddle the patient's nose, which provides an intuitive alignment strategy and suits a diverse range of patient sizes.

However, the prior art eye drop administration aides have several problems. Firstly, prior art devices are equipped with only one locating feature with which to help align the dispensing tip of the medicine bottle over the eyes. Whenever a patient must sequentially administer drops into their two eyes (e.g., the right eye then the left eye), the patient must rotate the apparatus or twist her hands when transferring the apparatus from the first eye to the second eye. Such a twisting or transferring motion can be uncomfortable or cumbersome for any patient, but is especially problematic for patients with fine motor skill issues, poor eyesight issues and those with high anxiety concerns. Furthermore, moving and repositioning the eye drop bottle between the two eyes substantially increases the risk of wasting drops and/or contaminating the patient's eyes. Another issue is that the prior art locator features that reference off the patient's nasal bridge tend to protrude dangerously close to the patient's eye inner corners which are very sensitive areas (e.g. Medial Canthus) where an upper and lower eyelids meet and may cause the eye to blink untimely. Furthermore, prior art locator features that merely straddle the patient's nasal bridge are susceptible to inadvertently sliding up or down the nose, thereby causing misalignment of the placed eye drop.

The prior art has attempted to address the inherent problems associated with moving and repositioning the eye drop bottle between the two eyes by adapting a swiveable or rotatable mechanism. Examples of such prior art apparatus may be seen in U.S. Pat. No. 8,348,912 to Rehkemper issued Jan. 8, 2013, and U.S. Pat. No. 5,569,224 to Michalos issued Oct. 29, 1996. In these examples, a part holding the bottle can be swiveled or rotated in moving from the first eye to the second eye. However, there are still several drawbacks to these mechanized devices. When rotating the swivelable part from a first eye to a second eye, the patient still must twist their hand. Moreover, the patient's free hand is required to hold the apparatus during the rotation procedure which in effect means that the apparatus requires two handed operation—a difficulty for some patients. Secondly, the swiveling part is at high risk of swinging out of position just as the patient attempts to self-administer an eye drop thereby wasting one or more drops of medicine. A self-administering patient cannot easily hold steady the swiveling part with their free hand and at the same time pull down the lower eyelid. In addition, the swivelable mechanism increases manufacturing costs.

There is therefore a long-felt yet still unresolved need for a patient to self-administer medicated eye drops into both eyes using only one hand and in such a manner that medicated drops are not wasted. The eye drop assist device and method must be easily executed by patients that lack fine motor skill issues, suffer from poor eyesight and those with high anxiety concerns. Caregivers must also find such an assist device or method easy to use, intuitive to operate and preferably ambidextrous. Accordingly, there exists a need for an improved eye drop assist apparatus and method for sequentially administering ocular medication to a patient's two eyes that overcomes the inherent disadvantages and shortcomings of the prior art.

BRIEF SUMMARY OF THE INVENTION

According to one aspect of this invention, an eye drop assist apparatus is capable of sequentially administering an ocular medication from the tip of an eye drop bottle to a patient's two eyes. The two eyes are separated from one another by a pupillary distance. The apparatus comprises a holder. The holder defines a bottle support axis. The holder is configured to support the eye drop bottle so that the bottle tip is disposed along the bottle support axis. A first nasal locator is connected to the holder. The center or apex of the first nasal locator extends laterally from the bottle support axis a first offset distance. The first offset distance is generally equal to one-half the pupillary distance. A second nasal locator is connected to the holder and its center or apex is spaced symmetrically on the other side of the holder from the first nasal locator. The center of the second nasal locator extends laterally from the bottle support axis a second offset distance. The second offset distance is generally equal to one-half the pupillary distance.

According to another aspect of this invention, a method for sequentially administering ocular medication from the tip of a bottle to a patient's two eyes comprises the steps of placing the bottle into an eye drop assist apparatus having a first and a second nasal locators, abutting the first nasal locator against a patient's nose while concurrently aligning the tip of the bottle directly over a first eye of the patient, squeezing the bottle to forcibly expel at least one drop of ocular medication into the first eye, linearly translating the bottle so that the second nasal locator abuts against the patient's nose while concurrently aligning the tip of the bottle directly over a second eye of the patient, and squeezing the bottle again to forcibly expel at least one drop of ocular medication into the second eye.

The present invention overcomes the disadvantages and shortcomings of the prior art by providing an improved eye drop assist apparatus and method for sequentially administering ocular medication to a patient's two eyes. The apparatus and method enables a patient or caregiver to administer medicated eye drops into both eyes using only one hand and in such a manner that medicated drops are not wasted. Two distinct nasal locators (first and second) are situated relative to the dispensing tip of the bottle so that a simple linearly translating motion of the patient's (or caregiver's) hand effects both drop placements. This simple motion can be accomplished by those with impaired fine motor skill. The eye sight of the person administering the medicated eye drops can be very poor with the present invention (even blind for self-administered applications), and yet place eye drops perfectly in both eyes because the two nasal locators are spaced apart from the bottle axis (i.e., dispensing tip) each by an offset distance that is generally equal to one-half the pupillary distance. This means that movement of the apparatus and medicated bottle follows the straight-line distance between the patient's two eyes. In other words, the shifting movement of the eye drop bottle perfectly coincides with the patient's innate sense of the distance between their own two eyes, thus making this apparatus and method far more intuitive than any prior art technique. This innate aspect is combined with the fact that a patient will consider it easy to find the top of the bridge with the V-shaped nasal locator. The distance from the nose and the way to place the nasal locator at the top of the bridge makes it easier to accomplish than just holding the bottle over the eye. A user can feel when the hook of the nasal locator is moved over the patient's nose. Furthermore, the linear translating movement required to move the bottle from the first eye to the second eye can be easily accomplished by either hand, making this apparatus and method truly ambidextrous.

BRIEF DESCRIPTION OF THE SEVERAL VIEWS OF THE DRAWINGS

These and other features and advantages of the present invention will become more readily appreciated when considered in connection with the following detailed description and appended drawings, wherein.

DETAILED DESCRIPTION OF THE INVENTION

Referring to FIGS. 1-5, wherein like numerals indicate like or corresponding parts throughout the several views, an eye drop assist apparatus is generally shown at 10 for use administering medicated eye drops. The apparatus 10 is adapted to consecutively administer eye drops in both eyes of a patient in a natural, easy and intuitive manner without wasting eye drops or aggravating the patient. In particular, the person applying the drops (who may or may not be the patient who receives the drops) can do so with one hand and without the need to twist or contort the administering hand as the apparatus moves from one eye to the next.

Figure 1:
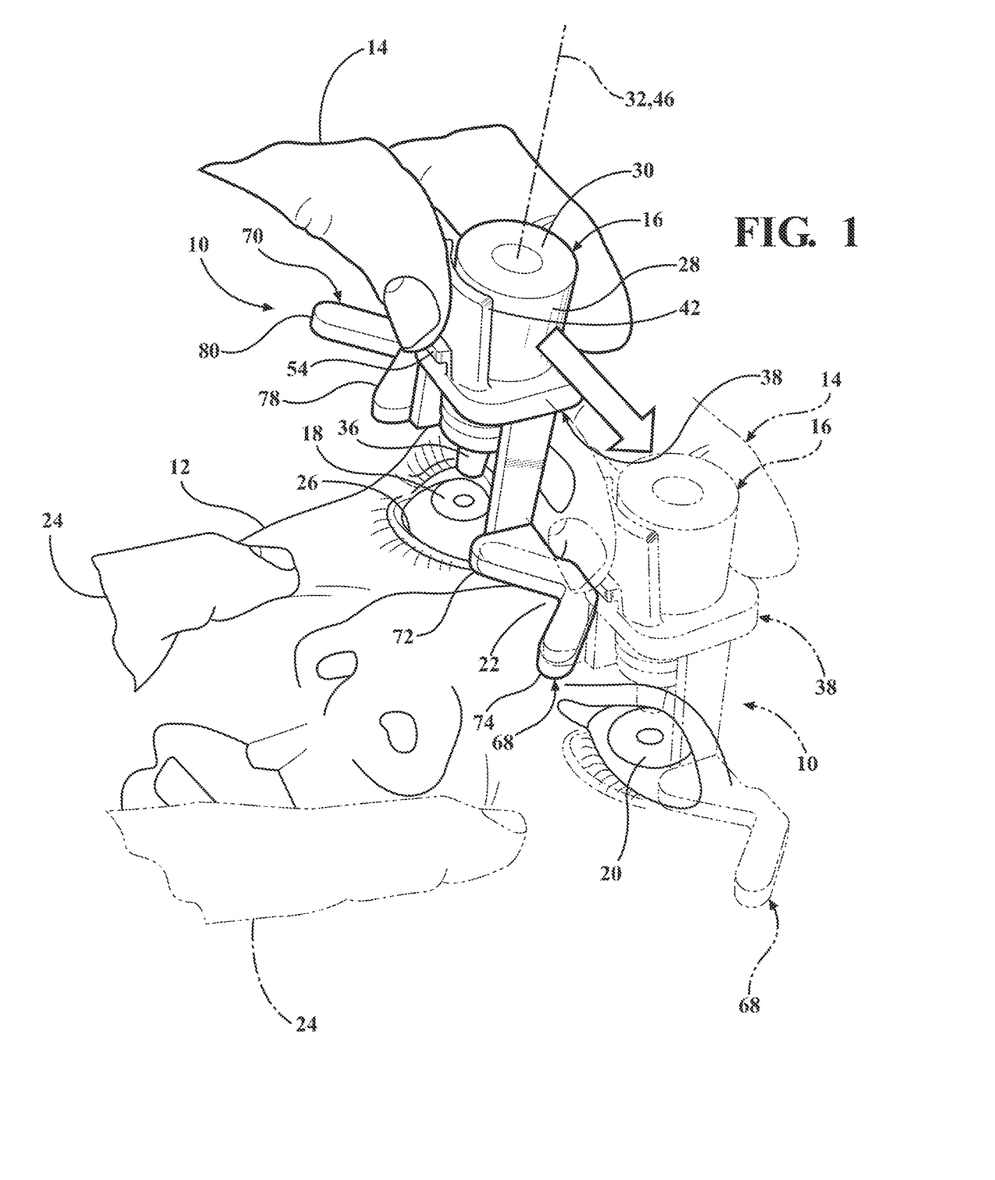
FIG. 1 depicts a user holding an eye drop assist apparatus according to one embodiment of the present invention, with subsequent movement to administer drop in a second eye shown in phantom lines.

FIG. 1 depicts the eye drop assist apparatus 10 in use. A patient, generally indicated at 12, receives medicated eye drops utilizing the apparatus 10. The drops are administered as needed or according to a prescribed dosage. The apparatus 10 can be manipulated directly by the patient 12 or by a caregiver. For convenience, a person who administers eye drops using the apparatus 10 will be referred to as a user, it being understood that the user can be either the patient 12 or a caregiver. The user holds the apparatus 10 in one hand 14. The one hand 14 can be either the user's left hand or right hand according to the user's preference, but is depicted in FIG. 1 as a right hand 14. An eye drop bottle containing liquid eye medicine (or soothing agent), generally indicated at 16, is supported in the apparatus 10.

The patient 12 is shown having a first eye 18 and a second eye 20. The first eye 18 can be either the patient's right or left eye, with the second eye 20 being the other. A distance between the center of the first eye 18 and the center of the second eye 20 is commonly known as a pupillary distance. The average adult male pupillary distance is 60 mm. The average adult male and female pupillary distance is not substantially different; however these measures can change from person-to-person and are generally much smaller for children. An area of a nasal bridge 22 is found between the inside corners of the eyes 18, 20. The nasal bridge 22 forms a top or upper part of the nose of the patient 12. The nasal bridge 22 is generally utilized as a reference point for abutting the apparatus 10 as will be described. When the lower eyelids are pulled down with a free hand 24 as shown in FIG. 1, a conjunctival sac 26 is exposed between each eyelid and its associated eyeball. Ophthalmologists often recommend to administer medicated eye drops directly into the conjunctival sac 26 instead of aiming the drops onto more sensitive points of the eye 18, 20 such as the cornea. One-hand 14 operation of the apparatus 10, therefore, is desirable for the user to administer the eye drops toward the conjunctival sac 26 since the free hand 24 can be used to lower the eyelids.

Figure 2:
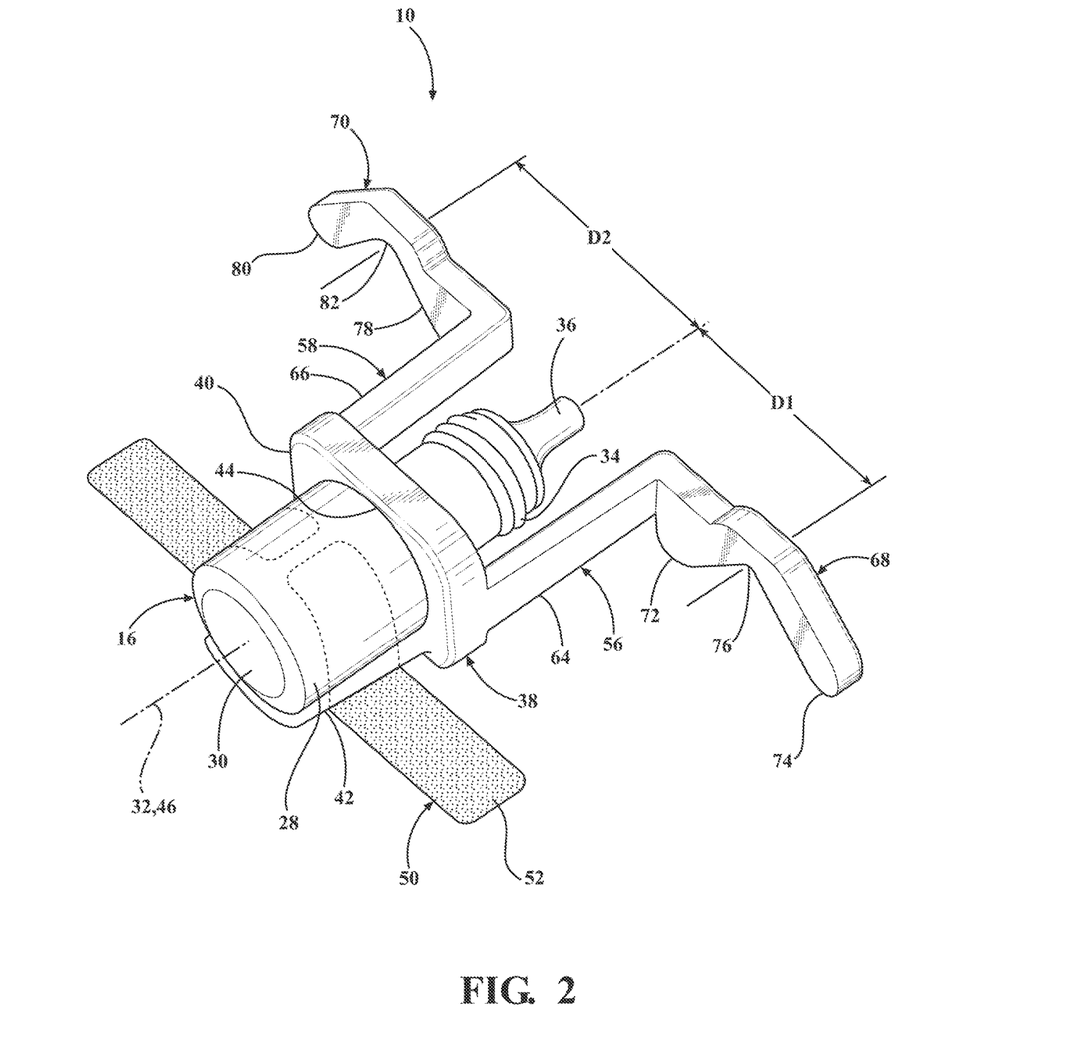
FIG. 2 is a perspective view of the eye drop assist apparatus.
Figure 3:
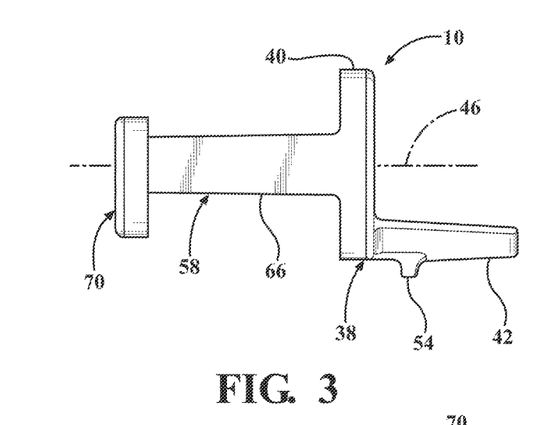
FIG. 3 is a left side view of the eye drop assist apparatus, it being understood that the right side view is a substantial mirror image thereof.
Figure 4:
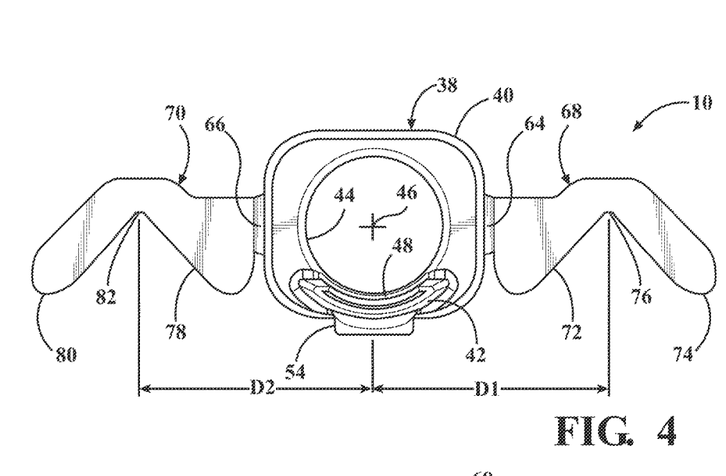
FIG. 4 is a front view of the eye drop assist apparatus.

The apparatus 10 is adaptable for use with any style of bottle 16, including most if not all commercially available types. FIGS. 1 and 2 illustrate one specific bottle 16 configuration for illustrative purposes only. In the illustrated examples, the bottle 16 has a semi-flexible body 28 having a generally hollowed cylindrical shape that extends axially between a base 30 and a shoulder (not shown). A bottle axis 32 is defined longitudinally through the approximate center of the body 28. A threaded neck 34 extends axially from the shoulder and is adapted to receive a bottle cap (not shown). A dispensing tip 36 extends axially from the threaded neck 34 along the bottle axis 32 and is provided with an orifice to expel a drop of ocular medication when the body 28 is squeezed.

FIGS. 2-5 depict one preferred embodiment of the apparatus 10. The apparatus 10 comprises a holder 38 and first 56 and second 58 nasal locators. The holder 38 supports the bottle 16 and also provides a convenient grasping point for the one hand 14 in use. Preferably, the holder 38 allows the user to connect any style of bottle 16 securely in the apparatus 10. This can be accomplished by many various techniques in addition to the one(s) shown in the accompanying illustrations. According to one illustrated method, the bottle 16 is secured in the holder 38 via a collar 40 and grip 42 features. In this specific example, the collar 40 has a four-cornered plate shape and each corner is formed with a generous round-over to provide a smooth, comfortable tactile feel when handled. Perhaps best shown in FIG. 4, the collar 40 includes a hole 44 centered along a bottle support axis 46. The bottle support axis 46 is an imaginary axis that runs through the center of the hole 44 and is oriented perpendicularly to the body of the collar 40. When the bottle 16 is operatively attached to the apparatus 10, the bottle axis 32 generally coincides with the bottle support axis 46 as shown in FIGS. 1 and 2. The collar 40 thus supports the body 28 of the bottle 16. Notwithstanding the illustrated embodiments, it should be emphasized that the collar 40 can be configured in any shape needed to support any style of bottle 16. The hole 44 also can be any shape—closed or open or segmented—corresponding to any cross-sectional shape of the bottle 16. The hole 44 need not have a fixed inner periphery, but could be elastically flexible or circumferentially adjustable to constrict about the bottle 16 for better retention. The thickness of the collar 40 (along the bottle axis direction) can also be adjusted to make the bottle 16 snap into place. Eye drop bottles generally have a bottle ridge between the threaded neck 24 and the shoulder so the collar 40 can be made to be an appropriate thickness matching this distance between the bottle ridge and the body of the bottle so that the bottle 16 can snap into place.

The grip 42 protrudes in cantilever fashion from one side edge of the collar 40. In the illustrated examples, the grip 42 is shown having a generally concave plate with an arcuate curve centered about the bottle support axis 46. The grip 42 helps support the bottle 16 so that it remains approximately perpendicular to the collar 40 during use. As the body 28 of most medicated eye drop bottles 16 is rounded or at least curved, the grip 42 may be formed with a concave cradle surface 48, as shown best in FIG. 4. The curvature of the cradle surface 48 may match or align with the curved inner periphery of the hole 44. The cradle surface 48 is intended to secure most commercially available shapes of bottles 16 so that the position of the bottle 16 does not shift relative to the apparatus 10 in use. If the bottle 16 shifts in use, there is a risk that the dispensed eye drop will miss the intended point of aim and possibly even miss the eye 18, 20 altogether. As shown in FIG. 2, an elongated adhesive strip, generally indicated at 50, may be wrapped around the bottle 16 and the grip 42 for increased security. The adhesive strip 50 has an adhesive side 52 that will concurrently adhere to the bottle body 28 and the outer surface of the grip 42 to mechanically secure the bottle 16 with the apparatus 10. The grip 42 also can function as a way to hold the bottle 16 in place between the user's thumb and finger holding the bottle body 28 against the grip 42. The grip 42 with the user's fingers helps prevent the bottle 16 from twisting around the bottle axis 32 in the apparatus 10. If the bottle 16 were permitted to twist around the bottle axis 32, then the bottle tip 36 may move away from the intended location over the eye. These features, such as the grip 42 being held by the thumb/fingers as well as with the adhesive 50, therefore prevent undesirable bottle twist. Instead of the adhesive strip 50, a cable tie (not shown) can be applied to secure the bottle 16 with the apparatus 10. The cable tie may be wrapped around the bottle 16 and the grip 42 so as to secure the bottle 16 so that the bottle 16 does not twist around the bottle axis 32 in the apparatus 10.

In the illustrated embodiment, the grip 42 is shown further including a ridge 54. As perhaps best shown in FIG. 1, the thumb of the user's one hand 14 may find enhanced traction by pressing against the ridge 54 while manipulating the apparatus 10. The ridge 54 protrudes generally perpendicular from an outer or bottom surface of the grip 42. While many designs of the ridge 54 are certainly possible to enhance a user's tactile grip on the apparatus 10 (e.g., corrugations or rubberized areas) one specific example of the ridge 54 is shown having an oblong rectangular shape. When the cable tie is applied to hold the bottle 16 rather than the adhesive strip 50, the cable tie may be disposed between the collar 40 and the ridge 54 so that the ridge 54 helps prevent the cable tie from sliding off the grip 42.

In yet another alternative embodiment, an O-ring or elastic band (not shown) can be used instead of or in addition to either of the previously described methods of securing the bottle 16 in the apparatus 10. According to this latter embodiment, the O-ring is placed on the bottle 16 between the bottle shoulder and the bottle ridge. In one specific example, the O-ring is stretched over the neck of the bottle and positioned between the bottle shoulder and the bottle ridge. If the outer diameter of the O-ring is suitably small, the O-ring will frictionally fit into the hole 44 effectively wedging itself in place to establish a tight frictional fit that will restrain the bottle 16 in the hole 44. If the diameter of the O-ring is sufficiently large, the O-ring will act as a keeper or shim between the collar and the bottle ridge effectively preventing the bottle from sliding back out of the hole.

Referring still to FIGS. 2-5, first and second nasal locators, generally indicated at 56 and 58, respectively, are symmetrically disposed on opposing sides of the holder 38, and even more specifically on opposite sides of the grip 42. The first 56 and second 58 nasal locators enable the user to locate the aim of each dispensed eye drop using the top of the nasal bridge 22 of the patient 12 as a point of reference. That is to say, the user aims the tip 36 of the bottle 16 toward the conjunctival sac 26 of each eye using the one hand 14 by alternately placing the first 56 and second 58 nasal locators against the patient's nasal bridge 22 as shown in FIG. 1.

Figure 5:
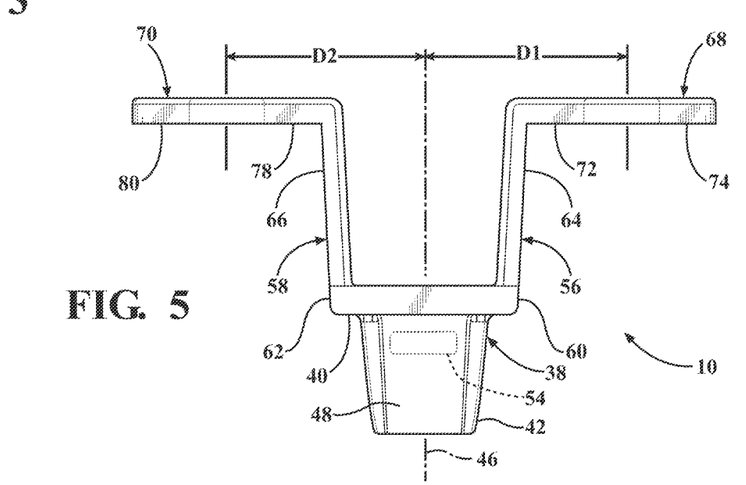
FIG. 5 is a top view of the eye drop assist apparatus.

As viewed from FIG. 5, the first nasal locator 56 is on the right-hand side of the holder 38 and comprised an L-shaped configuration composed of a first leg 64 and a first concave abutment 68. The first leg 64 extends predominantly axially from a first side edge 60 of the collar 40 on the opposite side from the grip 42. Located at a distal end of the first leg 64, the first concave abutment 68 juts outwardly or away from the bottle support axis 46. That is, the first leg 64 and the first concave abutment 68 together form the first nasal locator 56 as a right-angle formation. The first concave abutment 68 is perhaps best shown in FIGS. 1, 2 and 4 having an inverted "V" shape ideally suited to perch over the top of the nasal bridge 22 with little-to-no side-to-side slippage. In the illustrated embodiment, the first abutment 68 is formed by a first inside member 72 and a first outside member 74. The first inside 72 and first outside 74 members have generally short bar shapes that intersect at a first apex point 76 to establish the inverted "V" shape. The first inside 72 and first outside 74 members are preferably disposed in a common plane that is perpendicular (or generally perpendicular) to the bottle support axis 46. Of course, the first abutment 68 may be configured with other shapes to stably place the first nasal locator 56 around the top of the nasal bridge 22 such as a nose pad like that used in wire-frame eye glasses to name but one example.

Returning again to FIG. 5, the second nasal locator 58 may be configured as a mirror-image of the first nasal locator 56 on the left-hand side of the holder 38. In this manner, the second nasal locator 58 also has an L-shaped configuration composed of a second leg 66 and a second concave abutment 70. The second leg 66 extends generally parallel to the first leg 64, and the second concave abutment 70 juts outwardly or away from the bottle support axis 46 in a direction opposite to that of the first concave abutment 68. The second concave abutment 70 likewise has second inside 78 and second outside 80 members that intersect at a second apex point 82. Thus, the first 68 and second 70 concave abutments are generally co-planar and splayed in opposite outward directions. Each concave abutment 68, 70 is shaped with a substantially identical, albeit mirrored, configuration somewhat like an ASCII caret "^" to rest like a saddle over the top of the nasal bridge 22 of a patient 12. Preferably, the first 68 and second 70 concave abutments are symmetrically arranged relative to the holder 38 so that, in use, the user can conveniently move the aim point of an eye drop linearly from the first eye 18 to the second eye 20. That is, the balanced position of the first 76 and second 82 apex points enables the user to aim the tip 36 of the bottle 16 toward the conjunctival sacs 26 of the patient 12 when the nasal locators 56, 58 are respectively abutted on the nasal bridge 22 of the patient 12.

FIGS. 2 and 5 depict dimensional attributes of the respective first 68 and second 70 concave abutments relative to the bottle support axis 46. In particular, a first offset distance D1 is defined from the bottle support axis 46 to the first apex point 76. A second offset distance D2 is defined from the bottle support axis 46 to the second apex point 82. The first D1 and second D2 offset distances are generally equivalent to one-half the average pupillary distance which, as described above, is about 60 mm for an adult. Thus, an apparatus 10 intended for use by the average adult will have first D1 and second D2 offset distances equal to about 30 mm each (60 mm combined). Of course, the first D1 and second D2 offset distances may be adjusted to meet the needs of any intended patient that falls outside the average range, such as smaller first D1 and second D2 offset distances for pediatric applications. In an alternative embodiment (not shown), the first D1 and second D2 offset distances are adjustable.

The length of the first 64 and second 66 legs are designed so that the bottle tip 36 is held to a safe non-contact distance from the patient's eyes 18, 20 yet close enough that an eye drop will have a high rate of successfully reaching the eye even with a range of human error, actual size and proportion of the patient's face, degrees of a patient's head tilt, etc. In an alternative embodiment (not shown), the length of the first 64 and second 66 legs are adjustable to accommodate different bottle 16 sizes or other situational variables. As shown in FIG. 2, the relatively large gap between the first leg 64 and the second leg 66 may be designed to facilitate installation/removal of the bottle cap (not shown) when the bottle 16 remains securely held in the apparatus 10. Not only does this open gap allow placement of the bottle cap back on the bottle 16 while in the apparatus 10, it is also open enough of a space that the fingers will have room to take the cap on/off. This is part of why the legs 64, 66 are thin so that the fingers do not rub up against the legs 64, 66 as the cap is twisted on/off.

Returning to FIG. 1, the method for sequentially administering ocular medication to the patient's first 18 and second 20 eyes using the apparatus 10 will be described in detail. The bottle 16 is secured in the apparatus 10 with its cap removed. If the bottle 16 does not snap into place in the collar 40 and/or is not secured another way, then the added ways of attaching to the grip 42 should be applied (such as the adhesive tape 50, for example). The user takes hold of the combined apparatus 10 and bottle 16 with their one hand 14, gently holding the body 28 of the bottle 16 and grip 42 between thumb and forefinger (or perhaps other fingers). The user moves their hand 14 so as to position the first concave abutment 68 against the top of the nasal bridge 22 of the patient 12 as shown in solid lines in FIG. 1. This action automatically locates the bottle tip 36 directly over the first eye 18 of the patient 12 because the first offset distance D1 is approximately equal to one-half the patient's pupillary distance. The first concave abutment 68 is shaped so that its first inside 72 and first outside 74 members do not gouge into the sensitive corners of eyes 18, 20. That is, the co-planar orientation of the first inside 72 and first outside 74 members arranged perpendicular to the bottle support axis 46 allows the first concave abutment 68 to lie flat over the top of the nasal bridge 22, and thus maintain a safe separation from the patient's eye corners which are typically very sensitive. The free hand 24 preferably pulls down on the lower eyelid to hold open the first eye 18 so that the user can discharge the ocular medication directly into the conjunctival sac 26 by squeezing the bottle 16, preferably after the patient 12 has tilted his head back.

After discharging the ocular medication into the first eye 18, the user linearly translates the assembly 10 so that the second concave abutment 70 abuts against the top of the nasal bridge 22 as shown in phantom lines in FIG. 1. This simple, compact maneuver immediately brings the tip 36 of the bottle 16 over the second eye 20 so that a drop (or drops) of ocular medication can be placed into the second eye 20. It will be appreciated that the user places eye drops in each eye 18, 20 without changing hands or twisting the one hand 14. In this elegant economy of straight-line motion, the user is able to conveniently execute the administration of eye drop to the patient 12. In cases where the patient self-administers the drops, the apparatus 10 greatly facilitates this process by enabling one-handed operation that frees a second hand to pull down the eyelid for ideal drop placement in the conjunctival sac 26 region of the eyes 18, 20. Patients 12 that self-administer eye medication are frequently suffering from a medical condition that has rendered the eyes 18, 20 in discomfort or perhaps even impaired. As such, the apparatus 10 provides welcome assistance to quickly, intuitively align the bottle tip 36 directly over the eyes 18, 20 using largely touch senses at the nose bridge 22 and the one hand 14 so that operation is not hindered even in low light or poor vision situations. In another manner to position the first 68 or second 70 concave abutments against the top of the nasal bridge 22 of the patient 12, the user can put the first 76 or second 82 apex points over the tip of the nose and slide up the apparatus 10 to the top of the nasal bridge 22.

The linear translation of the bottle 16 and the apparatus 10 from the first eye 18 to second eye 20 provides several substantially significant advantages. The user is not required to change or twist the one hand 14 while administering eye drops from the first eye 18 to the second eye 20. This one-handed simple linear motion from the first eye 18 to the second eye 20 reduces the need to reconfigure the one hand 14 after placing the first drop to re-orient the tip 36 over the second eye 20. The novel method therefore makes it simpler to aim the tip 36 to the conjunctival sac 26 and reduce the risk of wasting the eye drops. The one-handed motion enables the user to make the best control of the apparatus 10 regardless of their dominant left-handed or right-handed orientation. That is, the apparatus 10 and method are completely ambidextrous because the straight-line motion between first and second eye applications matters not whether the user is left handed or right handed. The user than thus easily administers the prescribed amount of drops by simply controlling the strength applied to squeeze the bottle 16 using the user's preferred hand, with movement between first and second eye applications requiring only generally gross motor skills of the user's arm.

As mentioned above, the first 68 and second 70 concave abutments are positioned in a common plane that is perpendicular to the bottle support axis 46 so that the tip 36 of the bottle 16 will orient perpendicular to the first 68 and second 70 concave abutments in use. Thus, the apparatus 10 is designed so that the first 68 and second 70 concave abutments rest flat against the face of the patient 12 (i.e., not perpendicular to the nose) as shown in FIG. 1 when the tip 36 is aimed toward the conjunctival sac 26. This favorable flat or parallel disposition of the first 68 and second 70 concave abutments provides several advantages compared to prior art systems. The eye inner corners closest to the nose are a very sensitive area even for those with healthy eyes. The flat disposition prevents the inside 72, 78 and outside 74, 80 members from pushing down into the eye inner corners. The flat disposition allows the user to maintain the top of the nasal bridge 22 as a reference point to abut the first 68 and second 70 concave abutments regardless of the nose's shapes and sizes (i.e. some people's noses protrudes far or wide). Thus, the flat disposition can cup the top of the nasal bridge 22 and prevent the first 68 and second 70 concave abutments from sliding down farther on the nose, toward the tip of the nose. By comparison, a prior art design having a nose abutment feature that has a perpendicular disposition could be inadvertently slid up and down the nose bridge 22 more easily and thereby confuse where the tip 36 should actually be aimed. The flat disposition of the first 68 and second 70 concave abutments enables the apparatus 10 to stand upright on a flat table so that even when a bottle 16 is secured therein the assembly 10 can be stood upright on either the base 30 of the bottle 16 or on the first 68 and second 70 concave abutments.

Figure 6:
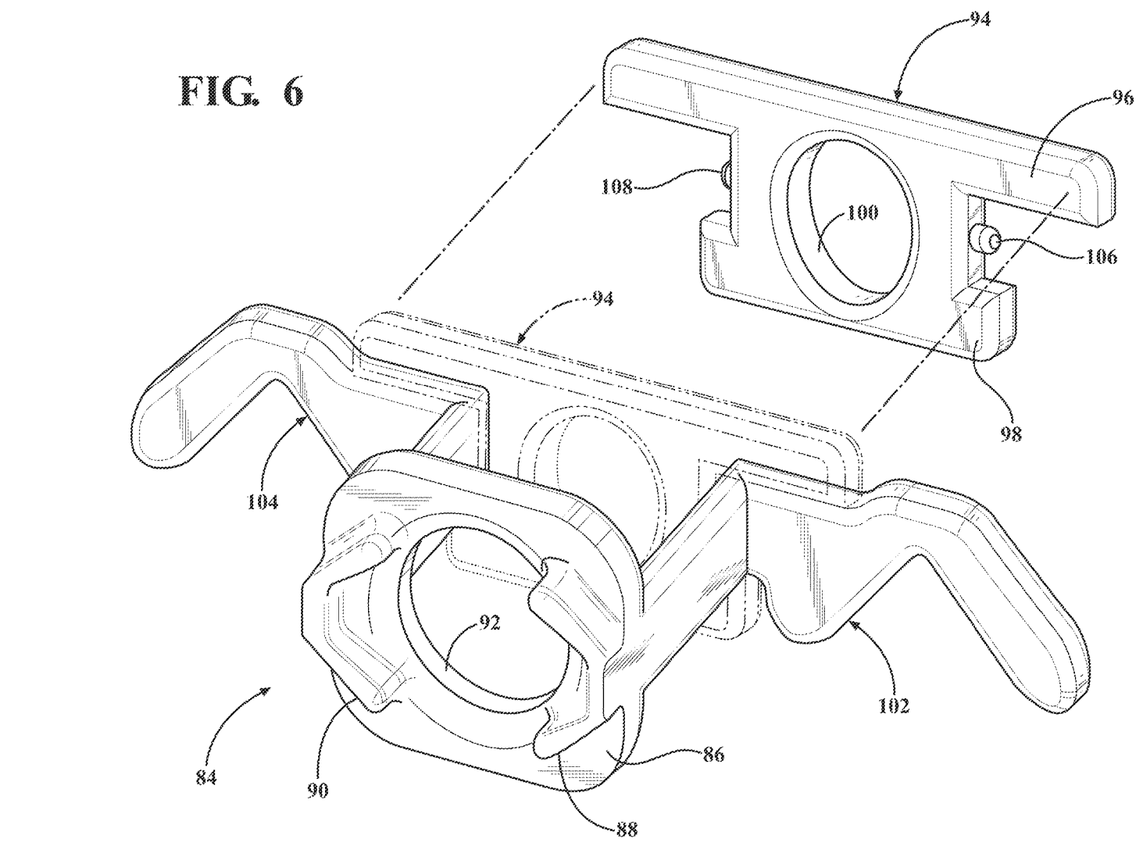
FIG. 6 is a perspective view showing a first alternative embodiment of the present invention wherein an optional guard is exploded away but shown connected to that apparatus in phantom lines.

FIG. 6 shows an alternative embodiment of the eye drop assist apparatus, generally shown at 84. The alternative apparatus 84 has many of the same structural features as the previously described apparatus 10, but is designed with increased bottle retention capability for bottle bodies that are elliptical in shape rather than circular and are able to snap into place, or held by friction, in the collar hole 92. While many designs of the alternative apparatus 84 are certainly possible to increase the bottle retention capability, one specific example of the alternative apparatus 84 is shown having at least two symmetric short grips 88, 90 on a collar 86. The first 88 and second 90 short grips are shown having a generally "C" shape in the form of brackets that protrude from the collar 86. The first 88 and second 90 short grips are disposed around a hole 92 for a medicine bottle (not shown). Although the first 88 and second 90 grips are shown as rigid features arranged symmetrically on opposite sides of the hole 92, it is certainly possible that they can be formed with elastic properties or made circumferentially adjustable or otherwise asymmetrically disposed around the hole 92 in any manner needed to snugly hold the bottle and prevent twisting about the bottle support axis.

When a bottle 16 is supported in the apparatus 84, the body and shoulder of the bottle plug into the hole 92 so that the first 88 and second 90 short grips abut with "interference fits" so that the shoulder and the body 28 of the bottle 16 is securely held within the apparatus 84. The interference fit is a frictional connection that is established when the parts are pushed together, rather than by any other means of fastening for example as seen in FIG. 2 with the adhesive strip 50. Said another way, the tip 36 of the bottle 16 goes through the hole 92, but not the body 28 or the shoulders of the bottle 16. The short grips 88, 90 cup the shoulders of the elliptical eye drop bottle body. Also, bottle grip may be accomplished by other methods than friction. For example, with snapping in place combined with the short grips 88, 90 keeping the bottle 16 from turning in place, this secures the bottle 16 in this design and keeps it from twisting. In one example adapted specifically to accommodate a 2.5 mL TravatanZ® eye drop bottle (not shown), the hole 92 may be approximately 16 mm in diameter with a fillet of about 2 mm radius. The first 88 and second 90 short grips and the body of the bottle are configured with interference fits to accept, tightly secure, and lock the bottle. It may be helpful to note that this configuration of the short grips 88, 90 works best if the collar 86 is made the correct thickness so that the bottle 16 snaps into the hole 92. Otherwise, even if the bottle 16 does not twist due to the short grips 88, 90, the apparatus 84 will just slide right off the bottle 16.

As shown in FIG. 6, an optional guard is generally indicated in 94. The guard 94 may be used to help prevent the dispensing tip of the bottle from contacting the eyes of the patient. Furthermore, the guard 94 provides the patient with a feeling of safety and comfort while the medicated eye drop is applied as well as a large circular aiming ring that will be visualized by the eye receiving the drop. While many shapes of the guard 94 are certainly possible, one specific example corresponding to the alternative apparatus 84 is shown having a generally rectangular shaped plate, including a top flange 96, a bottom flange 98 and a guard hole 100. The guard 94 is configured in line between a first concave abutment 102 and a second concave abutment 104. The guard hole 100 is disposed generally concentrically to the hole 92 of the apparatus 84 and allows the eye drop to fall through unhindered. The guard 94 may further include a first aligning pin 106 and a second aligning pin 108. The aligning pins 106, 108 protrude from the opposite sides of the guard 94 and are adapted to engage with corresponding grooves (not shown) in the apparatus 84. Many alternative types of aligning means (e.g., tongue-and-groove, wedge, or snap-latches) are certainly possible to facilitate fitting the guard 94 into the apparatus 84. Accordingly, the person of skill in the art will appreciate that the guard 94 may take various forms, as well as find application in any of the various embodiments of the apparatus.

Figure 7:
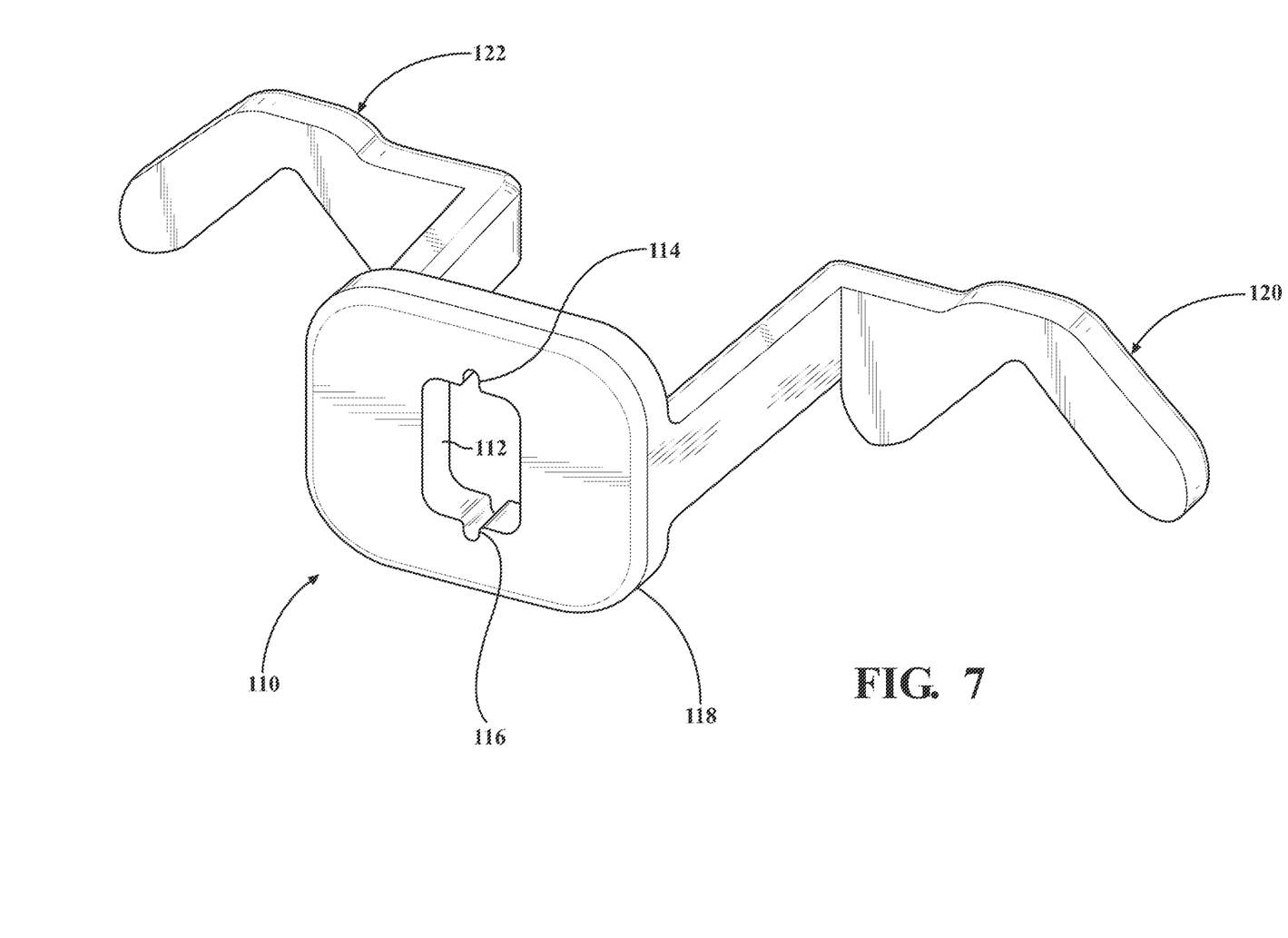
FIG. 7 is a perspective view showing a second alternative embodiment of the present invention.

FIG. 7 depicts a second alternative embodiment of the eye drop assist apparatus, generally shown at 110. The second alternative apparatus 110 has many of the same structural features as the previously described apparatus, but is designed to secure a single dose eye drop vial (not shown). Those of skill in the art will note that a hole 112 can be made any shape or size to fit any type of bottle, single-dose or otherwise. A single dose eye drop vial is a small container that retains a single dose (or few doses) of medicated eye drops. Thus, the vial is a form of bottle but intended for single-use applications. The vial typically has a semi-flexible hollowed shape with an orifice at its distal end and flanges along both long sides. While many designs of the second alternative apparatus 110 are certainly possible given the variety of vial shapes in the commercial market, one specific example of the alternative apparatus 110 is shown having the rectangular shaped hole 112, including a top slot 114 and a bottom slot 116 on the generally middle of a collar 118. The alternative apparatus 110 enables the user to insert the flanges of the vial into the top 114 and bottom 116 slots respectively so that the vial securely fits into the hole 112 and cannot be rotated in use. In a modified variation (not shown), more than two slots 114, 116 are symmetrically arranged around the hole 112 enabling the user to optimize the position of the vial.

The method for sequentially administering medicated eye drops from the vial to the patient's first and second eyes using the second alternative apparatus 110 is similar to the method described above using the apparatus 10. The vial is securely inserted in the alternative apparatus 110. The user takes hold of the vial with their one hand and moves the apparatus 110 so as to position a first concave abutment 120 against the top of the nasal bridge of the patient. This action automatically locates the vial orifice directly over the first eye of the patient. A free hand of the user or the patient preferably pulls down on the lower eyelid to hold open the first eye so that the user can discharge the ocular medication directly into the conjunctival sac by squeezing the vial. After discharging the medicated eye drops in the vial into the first eye, the user linearly translates the apparatus 110 so that a second concave abutment 122 abuts against the top of the nasal bridge. The linear translation action automatically locates the vial orifice directly over the second eye of the patient. The user then repeats the discharging action.

The foregoing invention has been described in accordance with the relevant legal standards, thus the description is exemplary rather than limiting in nature. For example, the first 56 and second 58 nasal locators could be designed to be foldable or separable from the holder 38 to facilitate portability of the apparatus 10. Likewise, variations and modifications to the disclosed embodiment may become apparent to those skilled in the art and fall within the scope of the invention.

What is claimed is:

1. An eye drop assist apparatus for sequentially administering ocular medication from an eye drop bottle having a dispensing tip to a patient's two eyes, the two eyes separated from one another, said apparatus comprising:
 a holder defining a bottle support axis, said holder configured to support the eye drop bottle so that the dispensing tip is disposed along said bottle support axis,
 a first nasal locator connected to said holder, said first nasal locator extending laterally from said bottle support axis a first offset distance, and
 a second nasal locator connected to said holder and spaced from said first nasal locator, said second nasal locator extending laterally from said bottle support axis a second offset distance equal to said first offset distance,
 wherein said first nasal locator is defined by a first concave abutment and said second nasal locator is defined by a second concave abutment, said first and second concave abutments including respective first and second apex points, said first and second offset distance measured from said bottle support axis to said respective first and second apex points, the distance between said first and second apex points equal to 60 mm.

2. The apparatus of claim 1, wherein the distance between said first nasal locator and said second nasal locator is equal to two times said first offset distance.

3. The apparatus of claim 1, wherein said holder includes a collar centered along said bottle support axis and oriented perpendicularly thereto, wherein said collar includes a first side and a second side, said first nasal locator including a first leg extending from said first side of said collar, said second nasal locator including a second leg extending from said second side of said collar.

4. The apparatus of claim 3, wherein said first leg is parallel to said second leg and parallel to said bottle support axis.

5. The apparatus of claim 4, wherein each of said first and second concave abutments extend radially from said bottle support axis, each of said first and second concave abutments being positioned symmetrically about said bottle support axis.

6. The apparatus of claim 5, wherein said first concave abutment has a V-shaped configuration, said second concave abutment having a V-shaped configuration.

7. The apparatus of claim 6, wherein each of said first and second concave abutments are disposed in a common plane perpendicular to said bottle support axis.

8. The apparatus of claim 6, wherein said V-shaped configuration of said first concave abutment is formed by a first inside bridge member and first outside bridge member, said V-shaped configuration of said second concave abutment is formed by a second inside bridge member and second outside bridge member, said first and second inside bridge members intersecting the respective said first and second outside bridge members at said respective first and second apex points, said first leg directly adjoining said first inside bridge member and said second leg directly adjoining said second inside bridge member.

9. The apparatus of claim 1, wherein said holder includes a collar centered along said bottle support axis and oriented perpendicularly thereto, wherein said holder includes a grip extending axially from said collar.

10. The apparatus of claim 9, wherein said grip has a concave cradle adapted to support the eye drop bottle.

11. The apparatus of claim 10, wherein said concave cradle has an arcuate curvature centered about said bottle support axis.

12. The apparatus of claim 10, wherein said grip includes a ridge disposed opposite said cradle.

13. The apparatus of claim 1, wherein said holder includes a collar centered along said bottle support axis and oriented perpendicularly thereto, wherein said collar comprises a circular hole extending through said collar.

14. A method for sequentially administering ocular medication from a bottle having a dispensing tip to a patient's two eyes, said method comprising the steps of:
   placing the bottle into an eye drop assist apparatus having a first and a second nasal locators,
   abutting the first nasal locator against a patient's nose while concurrently aligning the tip of the bottle directly over a first eye of the patient,
   squeezing the bottle to forcibly expel at least one drop of ocular medication into the first eye,
   linearly translating the bottle so that the second nasal locator abuts against the patient's nose while concurrently aligning the dispensing tip directly over a second eye of the patient, and
   squeezing the bottle again to forcibly expel at least one drop of ocular medication into the second eye.

15. The method of claim 14, wherein said step of placing the bottle further includes securing the bottle to the apparatus with at least one of an adhesive strip, a cable tie, and an O-ring.

16. The method of claim 14, wherein the patient's nose includes a nasal bridge disposed between opposing eye corners, wherein said step of abutting the first nasal locator includes directly contacting the top of the nasal bridge without directly touching the eye corners.

17. The method of claim 16, wherein said squeezing steps include discharging the ocular medication directly into the patient's conjunctival sac.

18. An eye drop assist apparatus for sequentially administering ocular medication from an eye drop bottle having a dispensing tip to a patient's two eyes, the two eyes separated from one another, said apparatus comprising:

a holder defining a bottle support axis, said holder configured to support the eye drop bottle so that the dispensing tip is disposed along said bottle support axis, a first nasal locator connected to said holder, said first nasal locator extending laterally from said bottle support axis a first offset distance, a second nasal locator connected to said holder and spaced from said first nasal locator, said second nasal locator extending laterally from said bottle support axis a second offset distance equal to said first offset distance, wherein said holder includes a collar centered along said bottle support axis and oriented perpendicularly thereto, wherein said collar includes a first side and a second side, said first nasal locator including a first leg extending from said first side of said collar, said second nasal locator including a second leg extending from said second side of said collar, said first leg is parallel to said second leg and parallel to said bottle support axis, said first nasal locator is defined by a first concave abutment and said second nasal locator is defined by a second concave abutment, wherein each of said first and second concave abutments extend radially from said bottle support axis, each of said first and second concave abutments being positioned symmetrically about said bottle support axis, said first concave abutment has a V-shaped configuration, said second concave abutment having a V-shaped configuration, each of said first and second concave abutments are disposed in a common plane perpendicular to said bottle support axis, and said first and second concave abutments includes respective first and second apex points, wherein said V-shaped configuration of said first concave abutment is formed by a first inside bridge member and first outside bridge member, said V-shaped configuration of said second concave abutment is formed by a second inside bridge member and second outside bridge member, said first and second inside bridge members intersecting the respective said first and second outside bridge members at said respective first and second apex points, said first leg directly adjoining said first inside bridge member and said second leg directly adjoining said second inside bridge member.

* * * * *